United States Patent
Maev et al.

(10) Patent No.: US 10,603,008 B2
(45) Date of Patent: Mar. 31, 2020

(54) ULTRASONIC DEVICE FOR ASSESSMENT OF INTERNAL TOOTH STRUCTURE

(75) Inventors: Roman Gr. Maev, Windsor (CA);
Eugene V. Malyarenko, Troy, MI (US);
Alexander Ilyutovich, Fort Lee, NJ (US)

(73) Assignee: Tessonics Corporation, Birmingham, MI (US)

( * ) Notice: Subject to any disclaimer, the term of this patent is extended or adjusted under 35 U.S.C. 154(b) by 2753 days.

(21) Appl. No.: 12/708,741

(22) Filed: Feb. 19, 2010

(65) Prior Publication Data
US 2010/0227295 A1 Sep. 9, 2010

Related U.S. Application Data

(60) Provisional application No. 61/153,759, filed on Feb. 19, 2009.

(51) Int. Cl.
*A61C 5/00* (2017.01)
*A61B 8/08* (2006.01)
*A61C 19/04* (2006.01)

(52) U.S. Cl.
CPC ............ *A61B 8/0875* (2013.01); *A61B 8/483* (2013.01); *A61C 19/04* (2013.01)

(58) Field of Classification Search
CPC ......... A61B 8/0875; A61B 8/483; A61B 6/14; A61B 6/5288; A61B 6/032; A61B 6/587; A61B 6/027; A61B 6/508; A61B 6/474; A61B 1/045; A61B 1/24; A61B 2576/00; A61B 8/58; A61B 8/4466; A61B 8/4483; A61B 8/5207; A61B 8/5269; A61B 8/56; A61B 8/14; A61B 5/055; A61B 19/50; A61B 19/5244; A61B 2019/262; A61B 2019/505; A61B 2019/507; A61B 5/0088; A61B 5/0086; A61B 1/063; A61B 1/0684; A61B 2576/02; A61B 2562/146; A61B 5/05; A61B 6/00; A61B 10/00; A61C 19/04; A61C 5/023; A61C 5/02; A61C 13/0004; A61C 3/00; G06Q 50/22; H04L 63/10; H04N 5/23293; G06F 3/04815; G06F 19/12; G06F 19/3437; G06F 19/321; G06F 19/327; G06T 17/10; G06T 15/08;

(Continued)

(56) References Cited

U.S. PATENT DOCUMENTS

| | | | | |
|---|---|---|---|---|
| 4,637,256 A | * | 1/1987 | Sugiyama ............ | G10K 11/352 433/215 |
| 4,762,002 A | * | 8/1988 | Adams ........................... | 73/625 |

(Continued)

*Primary Examiner* — Sean M Michalski
*Assistant Examiner* — Mirayda A Aponte
(74) *Attorney, Agent, or Firm* — Carlson, Gaskey & Olds, P.C.

(57) ABSTRACT

Example embodiments of this invention include a method and a device for assessing the internal structure of the tooth. In one example, the method is comprised of emitting a sequence of ultrasonic pulses from a given point on the tooth surface into the tooth at various directions of incidence (angles of incidence) with respect to the local tooth surface, recording the corresponding sequence of ultrasonic echoes from different internal dental formations, and processing the collected ultrasonic pulse-echo and pulse-direction data to present internal structure of the tooth in quantitative or graphical form.

19 Claims, 5 Drawing Sheets

(58) Field of Classification Search
CPC .............. G06T 19/00; G06T 2210/41; G06T 2219/008; G06T 19/20; G06T 7/0022; G06T 7/0065; G06T 2207/10116; G06T 2207/30036; G02B 21/367; G02B 27/58; G02B 21/0012; G02B 21/06; G02B 21/16; G02B 21/361; G02B 21/0004; G06K 9/00; G01N 29/04
USPC .. 433/215, 29, 72, 75, 119, 99, 22, 28, 102; 600/437, 589–591, 447, 439, 440, 300, 600/458, 103; 73/600, 627, 585, 587, 73/647, 648, 649, 633, 621, 618, 619, 73/620, 622, 623, 634; 367/87; 382/154, 382/128, 131; 378/38, 4; 348/36, 66; 15/4; 173/213, 216, 217
See application file for complete search history.

(56) References Cited

U.S. PATENT DOCUMENTS

| | | | | |
|---|---|---|---|---|
| 4,955,810 A * | | 9/1990 | Levy | A61C 19/04 433/114 |
| 5,874,677 A * | | 2/1999 | Bab | A61C 19/04 433/215 |
| 6,179,611 B1 * | | 1/2001 | Everett | A61B 5/0088 433/29 |
| 6,638,219 B1 * | | 10/2003 | Asch | A61B 8/00 433/214 |
| 6,719,692 B2 * | | 4/2004 | Kleffner | A61B 17/16 600/437 |
| 6,885,464 B1 * | | 4/2005 | Pfeiffer et al. | 356/602 |
| 6,971,991 B2 * | | 12/2005 | Lasser et al. | 600/437 |
| 7,010,150 B1 * | | 3/2006 | Pfeiffer et al. | 382/128 |
| 7,050,168 B2 * | | 5/2006 | Overbeck et al. | 356/407 |
| 7,285,091 B2 * | | 10/2007 | Blodgett | A61B 5/0088 433/215 |
| 7,286,954 B2 * | | 10/2007 | Kopelman et al. | 702/152 |
| 7,393,324 B2 * | | 7/2008 | Satoh | 600/437 |
| 7,477,925 B2 * | | 1/2009 | Lockhart et al. | 600/407 |
| 7,492,470 B2 * | | 2/2009 | Buchler et al. | 356/601 |
| 7,494,338 B2 * | | 2/2009 | Durbin et al. | 433/29 |
| 7,702,139 B2 * | | 4/2010 | Liang et al. | 382/128 |
| 7,748,273 B2 * | | 7/2010 | Halevy-Politch et al. | 73/627 |
| 7,855,354 B2 * | | 12/2010 | Eiff et al. | 250/234 |
| 7,912,257 B2 * | | 3/2011 | Paley et al. | 382/128 |
| 7,940,260 B2 * | | 5/2011 | Kriveshko | 345/419 |
| 7,974,453 B2 * | | 7/2011 | Wong et al. | 382/128 |
| 8,035,637 B2 * | | 10/2011 | Kriveshko | 345/419 |
| 2002/0012897 A1 * | | 1/2002 | Tingley | A61B 5/682 433/215 |
| 2004/0143186 A1 * | | 7/2004 | Anisimov | A61B 8/0875 600/437 |
| 2007/0037125 A1 * | | 2/2007 | Maev | A61B 8/0875 433/215 |
| 2007/0238996 A1 * | | 10/2007 | Lin | A61B 8/0875 600/437 |
| 2008/0234579 A1 * | | 9/2008 | Halevy-Politch | A61B 8/0875 600/439 |
| 2008/0241796 A1 * | | 10/2008 | Ce et al. | 433/215 |
| 2009/0143674 A1 * | | 6/2009 | Nields et al. | 600/437 |

* cited by examiner

ULTRASONIC DEVICE FOR ASSESSMENT OF INTERNAL TOOTH STRUCTURE

REFERENCE TO RELATED APPLICATIONS

The present invention claims priority to U.S. Provisional Patent Application No. 61/153,759, filed Feb. 19, 2009.

BACKGROUND

This invention relates generally to an ultrasonic diagnostic tool, and more specifically to a portable (handheld) ultrasonic 3-D imaging device for dental applications.

A dentist diagnosing a dental condition often relies on subjective data such as patient complaints, intraoral visual examination results, and results of selective physical probing. Unfortunately, this information is non-quantitative and relies heavily on dentist skill and experience.

Information about internal dental formations (tooth microanatomy) is useful for many reasons. For example, information about internal dental formations, such as distances to the enamel/dentine and dentine/pulp interfaces from the tooth surface, helps the dentist plan treatment. Measurements taken during drilling and other tooth processing techniques without significant interruption of the treatment process facilitate controlling the distance from the drill tip to internal structures of the tooth, (e.g., pulp). Monitoring the bond between restoration material and tooth tissue can identify failed bonds, which can cause caries or cavities in the interface between restoration material and tooth tissue (e.g., dentine). Monitoring the bond between a dental crown and the tooth also facilitates detecting and locating flaws, which can decrease the strength of the restored tooth or lead to caries or cavities under the crown.

Imaging systems, such as conventional X-ray diagnostics, often fail to provide comprehensive results. More sophisticated imaging systems, such as Optical-Coherent Tomography, Cone-Beam Tomography or Terahertz Pulse Imaging, are costly and complex. Further, as is known, the enamel and dentine layers that cover the pulp are irregularly shaped. Measurements of these layers with existing imaging systems are often inaccurate, especially around corners and inside restoration areas, due to internal dental formation interfaces being at a non-zero angle relative to the tooth surface.

SUMMARY

Example embodiments of this invention include a method and a device for assessing the internal structure of the tooth. In one example, the method is comprised of emitting a sequence of ultrasonic pulses from a given point on the tooth surface into the tooth at various directions of incidence (angles of incidence) with respect to the local tooth surface, recording the corresponding sequence of ultrasonic echoes from different internal dental formations, and processing the collected ultrasonic pulse-echo and pulse-direction data to present internal structure of the tooth in quantitative or graphical form.

The example proposed device includes a signal generator for forming ultrasonic signals, one or several transducers for emission and reception of ultrasonic pulses, position sensors for determining the angular position of the transducer, means for positioning of the transducer on the tooth surface, a receiver for acquiring and amplifying ultrasonic signals, an analog-to-digital converter for transforming signals and position sensors data to digital representation, and a computer for providing control of the device, signal and data processing, and visualization.

The example computer gives a quantitative presentation of the pulse-echo data with corresponding angles of incidence in the form of an A-scan or a sector scan. The latter can be transformed into a graphical 3-D presentation of the internal tooth structure. Also, the computer can calculate such parameters as thicknesses of the internal tooth layers, including enamel, dentin, and cementum, or distances to the interfaces between said internal layers from any point of interest on the tooth surface. In addition to presentation of the internal geometries of the tooth, the device may also calculate other geometric parameters based on the echoes from surrounding areas of the tooth, such as soft tissues, bone, periodontal pockets etc.

DETAILED DESCRIPTION OF THE PRESENTLY PREFERRED EMBODIMENT

Figure 1:
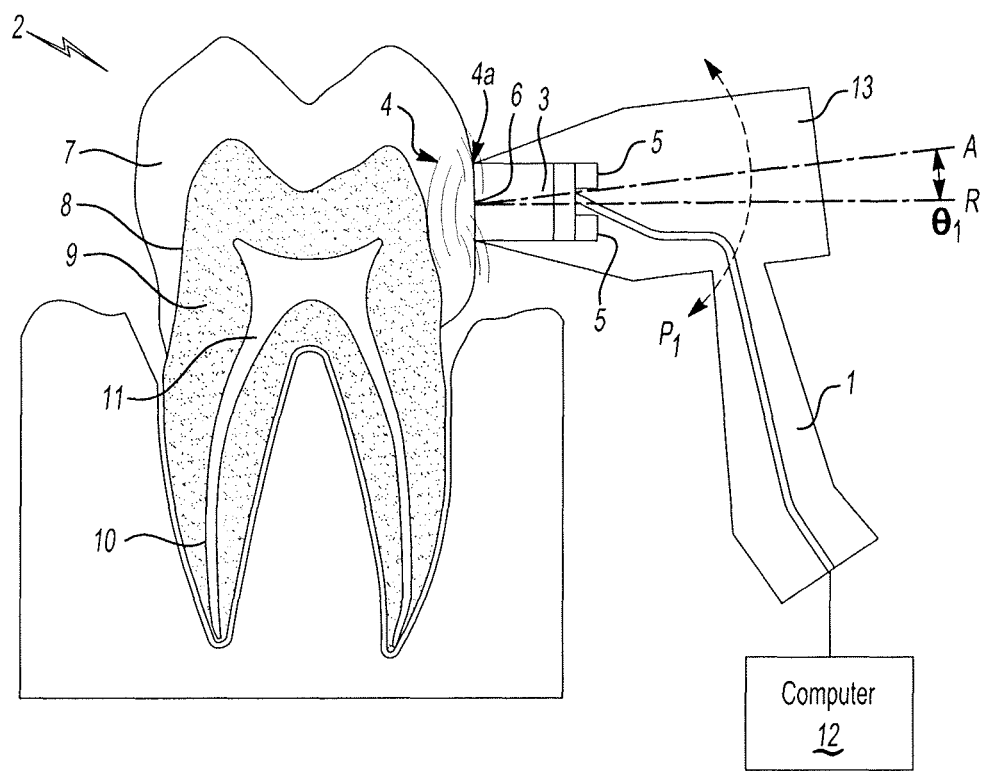
FIG. 1 shows a cross-sectional side view of a tooth and an example ultrasonic dental probe.
Figure 2:
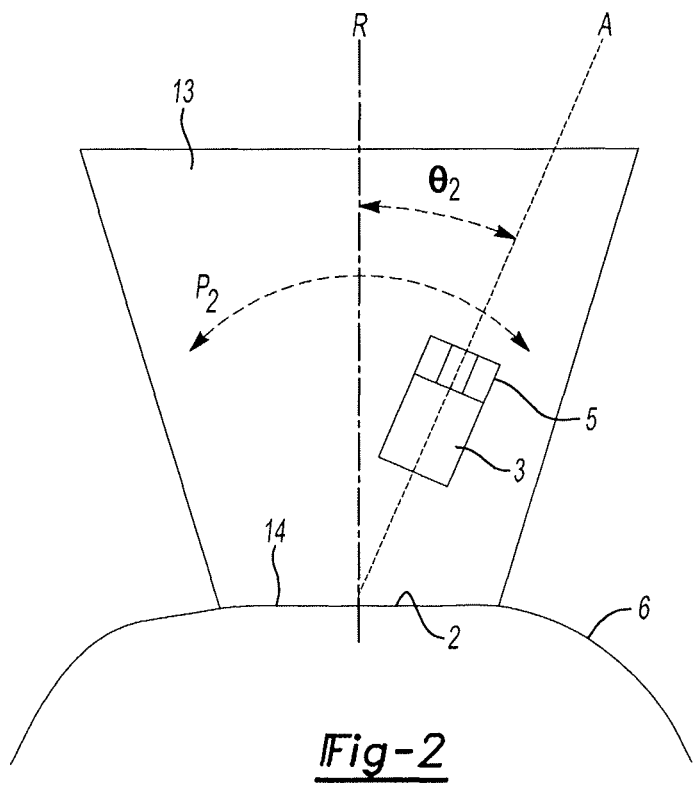
FIG. 2 shows a schematic top view of an example system for positioning a transducer of the FIG. 1 ultrasonic dental probe.

Referring to FIGS. 1 and 2, a handheld dental probe 1 is used to examine internal formations of a tooth 2. The dental probe 1 includes an ultrasonic transducer 3, which is configured to emit an ultrasonic pulse 4 into the tooth 2 at high frequency (e.g., 20 MHz or more), and position sensors 5.

Internal structures of the tooth 2 reflect the ultrasonic pulse 4 back to the dental probe 1 as reflected signals 4a. The reflected signals 4a (or echoes) received by the transducer 3 comprise reflections from various internal structures of the tooth 2, including an interface 8 between an enamel layer 7 and a dentine layer 9, and an interface 10 between the dentine layer 9 and a pulp layer 11. The thickness of a particular layer, or the distance to the corresponding interface (e.g. dentine-pulp interface), can be determined from the time of flight of the ultrasonic echo reflected by that interface.

In this example, the position sensors 5 are used to establish a direction of incidence of each ultrasonic pulse 4 based on at least two angles of deviation of a transducer axis A from a reference axis R. In this example, $\theta_1$ represents an angle of deviation in a vertical plane, and $\theta_2$ represents an angle of deviation in a horizontal plane. The reference axis R is established normal to a point of contact 6 between the tooth 2 and the probe 1 in one example.

The output data of the position sensors 5 ($\theta_1$ and $\theta_2$) is saved with the waveform of the reflected signals 4a on a computer 12. That is, the echo waveform is associated with angular coordinates $\theta_1$ and $\theta_2$, which indicate the direction of incidence of the ultrasonic pulse 4 that produced the echo, and saved.

In this example the angle position sensors are angular velocity gyro-sensors based on quartz crystals. A person skilled in the art and having the benefit of this disclosure would know how to incorporate such sensors into the probe 1. As known, such quartz-based crystals are used in electronic devices like digital and video cameras, handheld GPS navigation devices, etc.

In one example, the dental probe 1 is placed at some point of interest on the tooth surface during examination, and the dentist manually tilts the probe 1 along path $P_1$ for example, in different directions keeping fixed the point of contact 6 between the probe and the tooth.

In another example, an electromechanical tilting of the transducer 3 is implemented to automate the angular motion of the transducer 3 along path $P_2$ and systematically sample within a narrow 3-D sector in the neighborhood of the reference axis R. In such an example, the dentist holds the tip of the probe 1 against the tooth surface at 6, and the tilting mechanism (not shown) changes the ultrasonic incidence angle by tilting the transducer 3 with respect to the reference axis R in two mutually perpendicular planes. At each whole angle, an echo waveform is saved together with the two angles of the transducer 3 tilt. The stored collection of echo waveforms and angles can be ordered according to the values of the transducer tilt and readily displayed in the form of a volumetric sector scan (3-D image) or a sequence of plane sector scans (2-D images).

The electromechanical tilting may be implemented using a variety of techniques. In one example, the whole angle is sampled systematically by regular scanning along predefined trajectories. Another example randomly samples the whole angle. Since the required tilting range is relatively small, two piezo linear actuators may be used for both approaches.

A single spatial oscillator (spring based) is used to sample the whole angle in an uncontrolled fashion in one example. Other example actuators include mechanical actuators, piezo-bimorph actuators, magnetostrictive actuators, etc. The angular position of the probe, in one example, is derived from the actual or commanded displacement of the actuator(s). In another example, the angular position of the probe is derived from the angular position sensors either mounted directly on the probe or in contact with the probe.

In one example, acoustic contact between the ultrasonic probe and the tooth surface at 6 is maintained by providing a laminar water flow in the contact area. Certain hygienic coupling gels can be used as well. In another example, the ultrasonic coupling is provided with an elastic layer bonded to the contact surface of the ultrasonic probe.

If the automated tilting is implemented, the transducer 3 moves inside a housing 13 at the end of the handheld probe 1. The housing 13 is filled with water or gel in one example. An ultrasonically transparent membrane 14 covers an opening in the contact face of the housing 13 to facilitate establishing the acoustic coupling between the housing 13 and the tooth 2.

In this example, since stored ultrasonic waveforms are associated with the angular data determining the direction of the transducer 3 with respect to the reference direction R (e.g. normal to the tooth surface), the extracted distance to the interface 6 is also associated with a certain direction of propagation inside the tooth. Changing the angle of incidence by manually (or automatically) tilting the transducer 3 changes the direction of propagation inside the tooth 2 and thus the distances to the structural interfaces from the probe tip, calculated along the ultrasonic propagation path. This information can be relied upon to determine the nearest point of a given interface to the point 6 (at the tip of the probe). This information can be used to reconstruct spatial geometry of the internal tooth structures within the 3-D sector insonified by the ultrasonic transducer 3. Examination of this reconstructed geometry can reveal dental interfaces and help identify their closest points to the transducer tip, such as closest point of dentin/pulp interface (which, as known, is critical for monitoring the tooth drilling processes).

Figure 3:
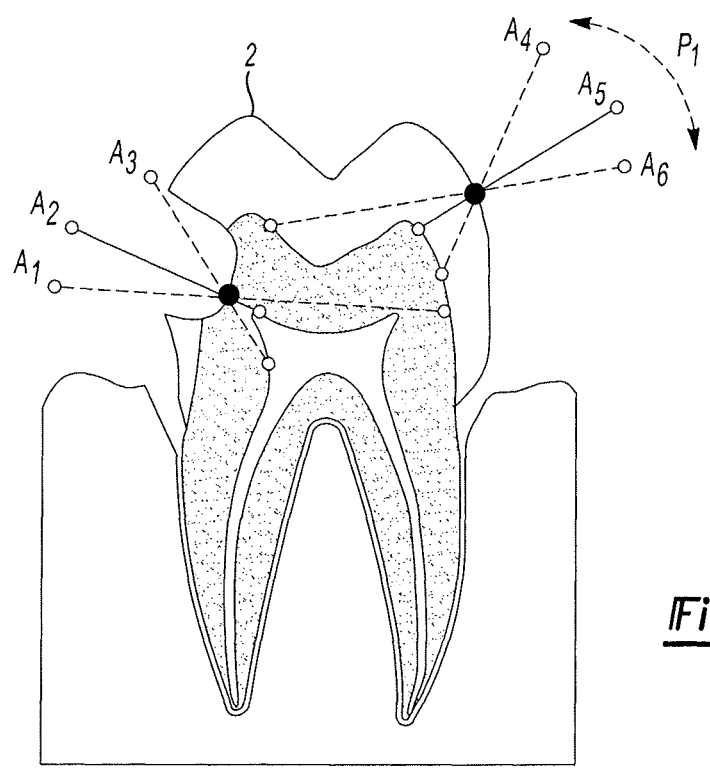
FIG. 3 shows example positions of the axis of the FIG. 1 ultrasonic dental probe relative to the tooth.

The volumetric sector scan approaches described herein provides more accurate measurements of the distance between the transducer tip and the chosen interface (e.g. dentine/pulp) than a single scan approach because, as shown in FIG. 3, the received echo of the prior art single scan approaches may not correspond to the nearest interface point for certain positions of the transducer axis $A_{1-6}$.

Figure 4:
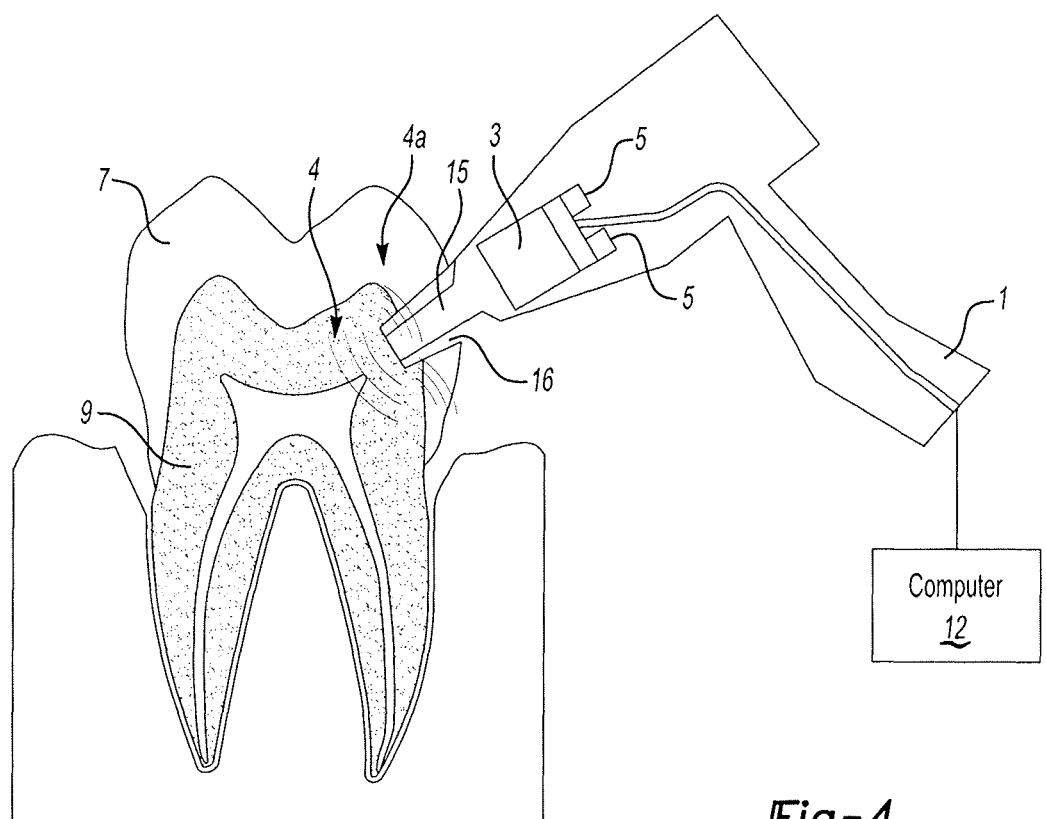
FIG. 4 shows a cross-sectional view of a tooth and an example ultrasonic dental probe having a cylindrical tip for monitoring a drilling process.

Referring to FIG. 4, an ultrasonic transducer 3 equipped with a cylindrical tip 15 produces the ultrasonic pulse 4 as the probe tip 15 inserted into the bore 16 advances the bore in the enamel layer 7 and part of the dentine layer 9 of the tooth 2 by drilling and removing tooth tissues. The thickness of the residual portion of the dentine layer 9 may be calculated from the acoustic time of flight between the bottom of the drilled bore 16 and the dentine-pulp interface, for example.

Figure 5:
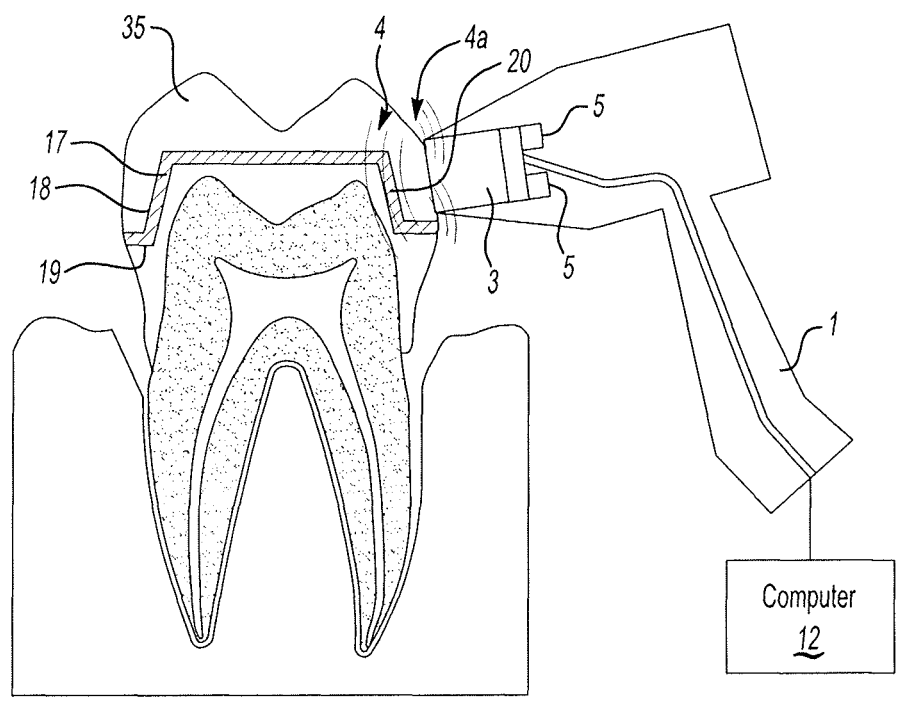
FIG. 5 shows a cross-sectional view of a crowned tooth and the FIG. 1 ultrasonic dental probe.
Figure 6:
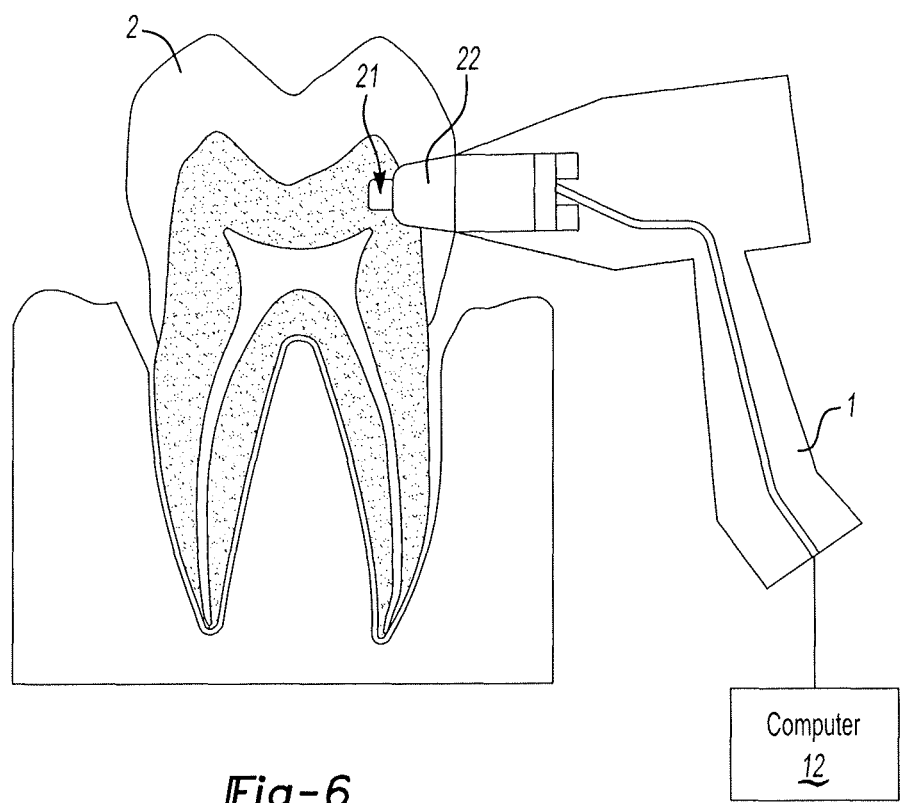
FIG. 6 shows a cross-sectional view of a filled tooth and the FIG. 1 ultrasonic dental probe.

Referring to FIG. 5, a crown-type dental prosthesis 35 attaches to the tooth 2 with a layer of adhesive 17 resulting in a crown-adhesive interface 18 and an adhesive-enamel interface 19. The ultrasonic transducer 3 mounted in the handheld dental probe 1 without the tip, or inside the probe 1 (FIG. 2) with the tip attached, directs the ultrasonic pulse 4 toward the tooth 2 and the crown 35. The crown-adhesive interface 18 and the adhesive-enamel or adhesive-dentine interface 19 both produce distinguishable echoes. Flaws or voids 20 in the adhesive can be located by interpreting amplitude increases and changes in the returning echoes of the ultrasonic pulse 4. For example, a distortion in the return echo may identify the adhesive void 20 or a shrinkage cavity 21 between the tooth 2 and the filling 22 (FIG. 6).

Figure 7:
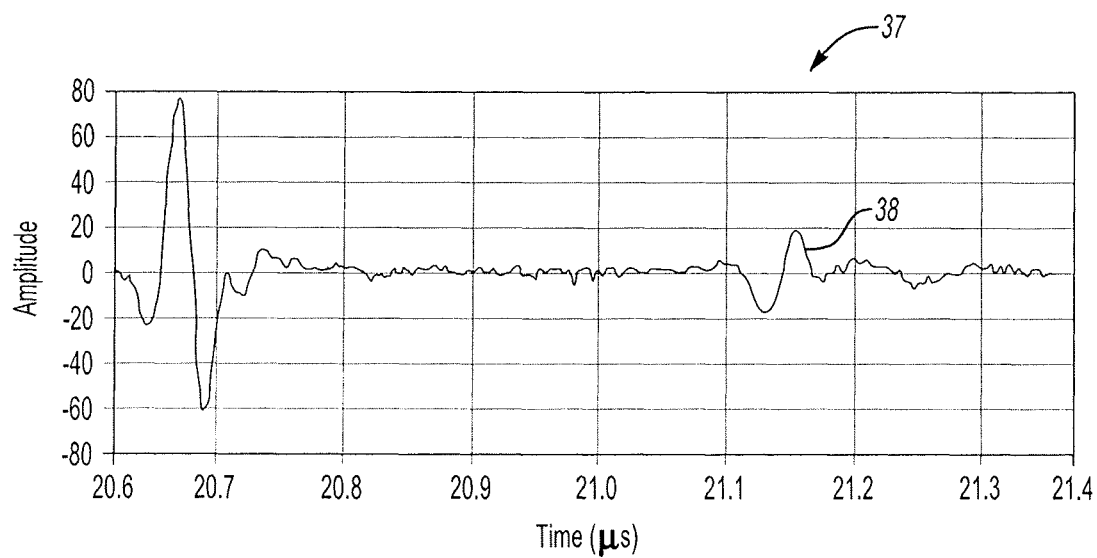
FIG. 7 shows example A-scans of a sample tooth.
Figure 8:
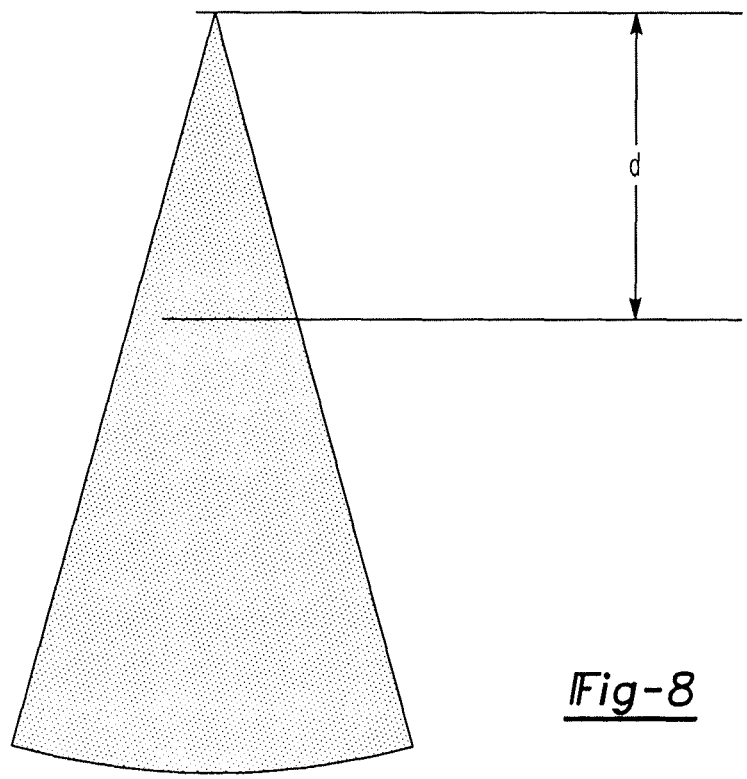
FIG. 8 shows an example sector scan identifying the pulp chamber.

FIG. 8 shows an example sector scan 39 from a tooth sample (in vitro). In this example, the distance d corresponds generally to the distance from the tooth surface to the pulp chamber. The sector scan 39 is a result of processing collected A-scans 37 (FIG. 7) and corresponding angle position data in a computer. Each such A-scan 37 corresponds to a particular value of the tilt angle and contains an echo from the tooth surface and subsequent reflections from internal structures. In this example the reflection 38 is from the pulp chamber. The distance d to the pulp chamber from the tooth surface is calculated as a product the time delay between respective echoes and the average speed of sound in the tooth material along the propagation path.

Figure 9:
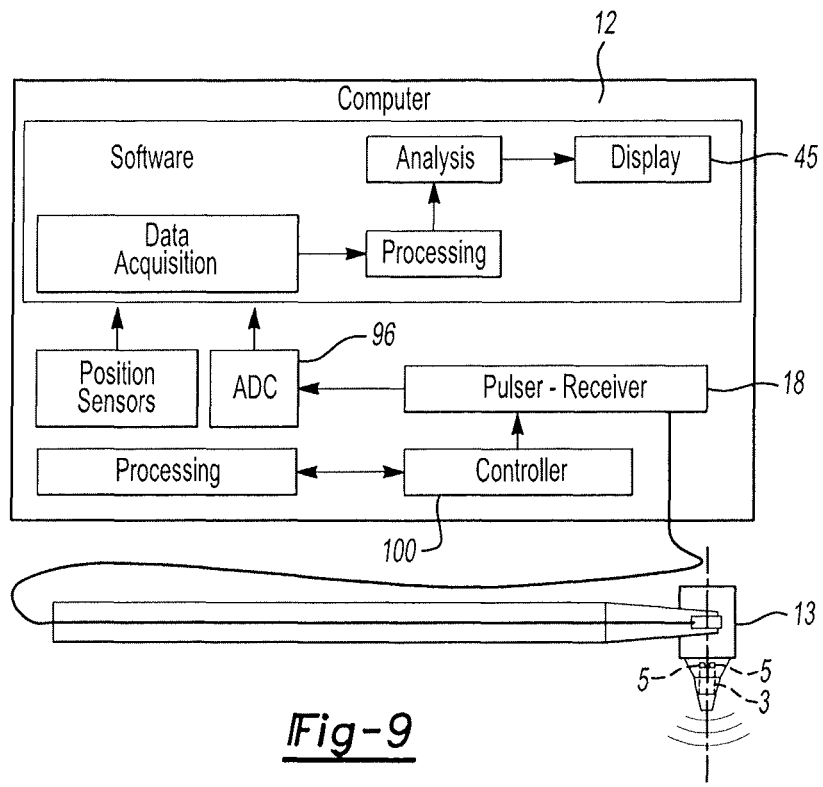
FIG. 9 schematically shows the flow of an example dental assessment system.

Referring to FIG. 9, the flow of an example proposed dental assessment system incorporates the handheld dental probe 1 with embedded angular position sensors 5 connected with computer 12. As shown, the ultrasonic transducer 3 and the angular position sensors 5 are bundled with the dental probe 1. Housing 13 is designed to allow for achieving varying angles of incidence of the ultrasonic pulse 4 to the contact area between the probe's tip and tooth surface by automatic or manual means.

To achieve maximum penetration of the ultrasonic pulse 4 into the tooth 2 when the dental layers are deposited parallel to interfaces, the axis X of the housing 13 should remain approximately perpendicular to the surface of the tooth 2. Surface irregularities of the tooth 2 may increase the difficulties in maintaining this position and may produce undesirable distorted echoes of the ultrasonic pulse 4 that should be properly treated. To avoid this, the operator may manually adjust orientation of the probe 1 until a better reference position is achieved.

Depending on the space constraints and handling needs, other many designs of the dental probe 1 may be used. For example, a tapered ultrasonic guide element, a cylindrical probe tip 15 (FIG. 4), a solid or elastic cone-shaped guide element, or a hollow solid or elastic cone-shaped guide filled with water or hygienic gel all may be used. To comply with bio-safety and hygienic standards, the handheld dental probe 1 typically incorporates bio-protection means, such as a sterilizable or disposable parts or a disposable sterile sleeve.

Since the proposed device is designed for operation at high ultrasonic frequencies (tens of MHz) that are strongly attenuated by most materials, the example ultrasonic probe is engineered to minimize the associated energy losses. This is achieved, in one example, by decreasing the length of propagation inside the probe and optimizing the acoustic coupling to the tooth surface. For example, a thin layer of elastic material (e.g. natural rubber, plastisol, etc.) may be adhesively bonded directly to the contact surface of the transducer tip. In another embodiment, such a layer is bonded to the contact surface of a (cylindrical or cone-shaped) delay line or a liquid-filled chamber where the transducer is electromechanically tilted. The thickness and material of said elastic layer may vary depending on the application needs and the acoustic properties of the material at the operating frequency.

The interchangeable housing 13 in the current examples facilitate maintaining the position of the probe 1 and directing the ultrasonic pulse 4 at the tooth 2. The shape of the housing 13 may be modified to enable access to certain hard to reach areas, e.g., between the teeth 2 or at the lower edge of the crown 10.

The dental probe 1 communicates signals from the ultrasonic transducer 3 to the pulser-receiver 18, and signals from the angular position sensors 5 to the conditioning circuit. An analog-to-digital converter 96 transforms the ultrasonic and angular position data to the appropriate digital format and transfers them through a controller 100 to a computer 12. The computer 12 processes and analyzes the input data and displays the results in a numerical or graphical form.

Figure 10:
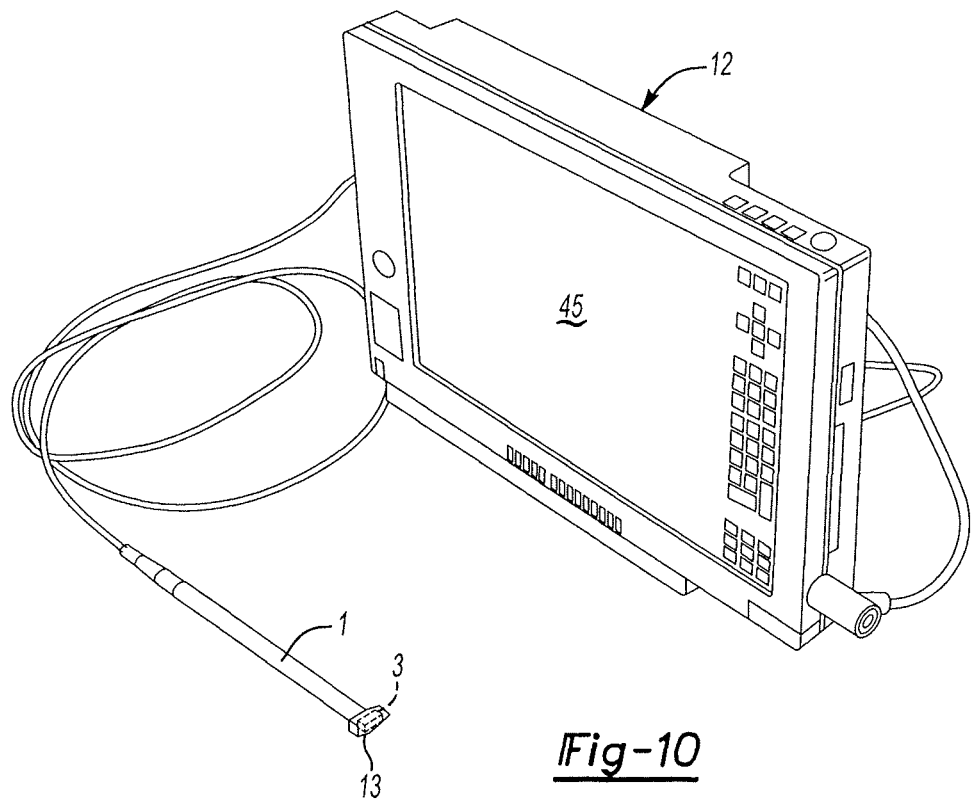
FIG. 10 shows a perspective view of an example dental diagnostic device.

FIG. 10 shows another example of the housing 13 incorporating an ultrasonic transducer 3 and mounted to the probe 1. The example computer 12 communicates with the pulser-receiver and angular position sensors (not shown) in the probe 1. When directed at the tooth 2 (FIG. 1), the computer 12 displays on a display 45, in real time and in a graphical format, the measurements of the tooth 2 based on the echoes from internal features of the tooth 2. In addition, the display 45 shows real-time visualization of the tooth 2 and any noted defects in the tooth 2, to facilitate real time examination of the tooth 2. In another example, the dental probe may be separately connected to an ultrasonic generator and a graphical display.

What is claimed is:

1. A method of evaluating a tooth structure, comprising:
   emitting, from a probe, a first signal from a first position;
   emitting, from the probe, a second signal from a second position that is different than the first position;
   determining an internal geometry of a tooth structure based at least on a reflection of the first signal and a reflection of the second signal; and
   contacting a surface of the tooth structure at a point of contact with the probe, and emitting the first signal and second signal during the contacting,
   wherein a reference axis extends away from the tooth structure in a direction normal to the surface of the tooth structure, the first signal and the second signal emitted in directions that are angled differently relative to each other and further angled differently relative to the reference axis.

2. The method of claim 1, wherein the first signal and the second signal propagate from a transducer of the probe along a transducer axis, and the step of determining further includes determining the geometry based at least on an angle of deviation between the transducer axis of the first signal and the reference axis, and an angle of deviation between the transducer axis of the second signal and the reference axis.

3. The method of claim 2, wherein the transducer is outside the tooth structure when emitting the first signal and when emitting the second signal such that no portion of the transducer is received within an area of the tooth structure.

4. The method of claim 1, wherein the internal geometry is a pulp layer of the tooth structure, and the step of determining further includes determining the shortest distance to the pulp layer from the point of contact.

5. The method of claim 1, wherein the tooth structure comprises a crown.

6. The method of claim 1, including emitting the first signal and the second signal from a common transducer of the probe.

7. The method of claim 1, including determining a two-dimensional sector of the tooth structure based on the first signal and the second signal.

8. The method of claim 1, including emitting a third signal from a third position that is different than both the first position and the second position, and determining a three-dimensional sector of the tooth structure based on the first signal, the second signal, and the third signal.

9. The method of claim 1, wherein the geometry of the tooth structure comprises an interface between a dentine layer and an enamel layer, or an interface between the dentine layer and a pulp layer.

10. The method of claim 1, including determining a thickness of a layer of the tooth based at least on a time of flight of the reflection of the first signal and a time of flight of the reflection of the second signal.

11. The method of claim 1, including emitting the first signal and the second signal from a common transducer within a probe housing of the probe, and tilting the transducer relative to the reference axis, the probe housing, and an internal structure of the tooth, the tilting after emitting the first signal and before emitting the second signal from the second position.

12. The method of claim 1, including emitting the first and second signals from a transducer of the probe and receiving the reflection of the first signal and the reflection of the second signal using the transducer.

13. The method of claim 1, wherein the first and second signals are ultrasonic pulses.

14. The method of claim 1, wherein the first signal is emitted from a transducer of the probe in a first direction that extends away from the transducer, and the reflection of the first signal travels in a second direction that extends toward the transducer.

15. The method of claim 1, further comprising, without rotating the probe about the reference axis, tilting the probe to move the probe from the first position to the second position, the tilting moving the probe with respect to the reference axis in two mutually perpendicular planes.

16. A method of evaluating a tooth structure, comprising:
emitting, from a probe, a first signal in a first direction from a first position;
emitting, from the probe, a second signal in a second direction from a second position, the second position different than the first position;
determining an internal geometry of a tooth structure based at least on a reflection of the first signal received by the probe and a reflection of the second signal received by the probe; and
contacting a surface of the tooth structure at a point of contact with the probe, and emitting the first signal and second signal during the contacting,
wherein a reference axis extends away from the surface of the tooth structure in a direction normal to the surface of the tooth structure, the first direction and the second direction angled differently relative to each other and further angled differently relative to the reference axis.

17. The method of claim 16, wherein the reflection of the first signal travels in a direction opposite the first direction, wherein the first and second signals are ultrasonic pulses.

18. The method of claim 16, further comprising, tilting the probe to move from the first position to the second position without rotating the probe about the reference axis.

19. The method of claim 16, further comprising emitting the first signal and the second signal from a transducer of the probe that is disposed outside the tooth structure such that no portion of the transducer is received within an area of the tooth structure.

* * * * *